(12) United States Patent
Gao et al.

(10) Patent No.: US 11,168,096 B2
(45) Date of Patent: Nov. 9, 2021

(54) METALLOPORPHYRIN COMPOUNDS, PREPARATION AND USES THEREOF

(71) Applicant: YUNNAN UNIVERSITY, Yunnan (CN)

(72) Inventors: Feng Gao, Yunnan (CN); Xudan Bi, Yunnan (CN); Yuechen Zhou, Yunnan (CN); Rong Yang, Yunnan (CN); Guokui Li, Yunnan (CN); Yan Li, Yunnan (CN)

(73) Assignee: YUNNAN UNIVERSITY, Kunming (CN)

( * ) Notice: Subject to any disclaimer, the term of this patent is extended or adjusted under 35 U.S.C. 154(b) by 0 days.

(21) Appl. No.: 17/134,404

(22) Filed: Dec. 26, 2020

(65) Prior Publication Data

US 2021/0198287 A1 Jul. 1, 2021

(30) Foreign Application Priority Data

Dec. 30, 2019 (CN) .......................... 201911387413.9

(51) Int. Cl.
*C07F 3/06* (2006.01)
*A61P 31/18* (2006.01)

(52) U.S. Cl.
CPC ................ *C07F 3/06* (2013.01); *A61P 31/18* (2018.01)

(58) Field of Classification Search
CPC ....................................................... C07F 3/06
USPC ....................................................... 514/185
See application file for complete search history.

(56) References Cited

U.S. PATENT DOCUMENTS 6,127,356 A * 10/2000 Crapo .................... A61K 31/00
  252/399
6,916,799 B2 * 7/2005 Fridovich ............ C07D 487/22
  514/183

FOREIGN PATENT DOCUMENTS

CN 109096339 A 12/2018
CN 109232663 A 1/2019

OTHER PUBLICATIONS

Venkatesh,, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Michael Y. Jiang and David Dolphin; Site-Specific Prodrug Release Using Visible Light; J.Am.Chem.Soc; Mar. 12, 2008.
Hilal Zengin Uzunmehmetoglu a, H. Yasemin Yenilmez a, Kerem Kaya a, Atif Koca b, Ahmet Altindal c, Zehra Altuntas Bayir a; Electrochemical, spectroelectrochemical, and dielectric properties of metallophthalocyanines bearing redox active cobalt and manganese metal centres; Inorganica Chimica Acta 459 (2017) 51-62.
Jean-Patrick Joly, Guillaume Mata, Patrick Eldin, Laurence Briant, Fabien Fontaine-Vive, Maria Duca and Rachid Benhida; Artificial Nucleobase-Amino Acid Conjugates: A New Class of TARRNA Binding Agents; Jan. 15, 2014; Chem. Eur. J.
Li Yan; Synthesis of luminescent transition mental complexes with high HIV reverse transcriptase inhibition activity; Jan. 15, 2020.

* cited by examiner

*Primary Examiner* — Nizal S Chandrakumar (57) ABSTRACT

This disclosure relates to pharmaceutical chemistry, and more particularly to a metalloporphyrin compound, and a preparation and application thereof. The metalloporphyrin compound is shown in formula (I), or an optical isomer, a pharmaceutically-acceptable salt or a solvate thereof, and can specifically recognize the HIV RNA and effectively inhibit HIV reverse transcriptase. This disclosure also provides uses of the compound in the preparation of a reagent for selectively recognizing HIV TAR RNA and a HIV reverse transcriptase inhibitor.

20 Claims, 5 Drawing Sheets

METALLOPORPHYRIN COMPOUNDS, PREPARATION AND USES THEREOF

CROSS-REFERENCE TO RELATED APPLICATIONS

This application claims the benefit of priority from Chinese Patent No. 201911387413.9, filed on Dec. 30, 2019. The content of the aforementioned application, including any intervening amendments thereto, is incorporated herein by reference in its entirety.

TECHNICAL FIELD

This application relates to pharmaceutical chemistry, and more particularly to a metalloporphyrin compound, and a preparation and uses thereof.

BACKGROUND

Acquired Immunodeficiency Syndrome (AIDS) seriously endangers human health, and in China, the new cases and deaths associated with AIDS are increasing year by year in 2012-2018. The latest data published by China Centers for Disease Control and Prevention revealed that as of the end of October in 2019, there were 958,800 surviving AIDS-infected cases in China. Impressively, AIDS has caused the most deaths among infectious diseases. Currently, human immunodeficiency virus (HIV) reverse transcriptase inhibitors have achieve a certain effect in the treatment and early prevention of HIV-related diseases (*Science*, 1992, 256, 1783-1790; *Biochemistry*, 2011, 50, 5042-5057), which indicates that the HIV reverse transcriptase can be considered as a primary target in the development of anti-AIDS drug (*Curr. Top. Med. Chem.*, 2004, 4, 1045-1057). Clinically, the commonly-used HIV reverse transcriptase inhibitors mainly include nucleoside reverse transcriptase inhibitors and non-nucleoside reverse transcriptase inhibitors. Nucleoside reverse transcriptase inhibitors are nucleoside analogs that can compete with viral DNA formed by reverse transcription of viral RNA to bind reverse transcriptase to inhibit the activity of reverse transcriptase to a certain extent. However, the long-term use of nucleoside reverse transcriptase inhibitors will cause serious side effects and obvious drug resistance, so this kind of inhibitors is greatly limited in practical application. Recently, some structurally-diverse small molecules have been found to have a good inhibitory activity against the HIV reverse transcriptase, and they are called non-nucleoside reverse transcriptase inhibitors due to the absence of a nucleoside structure. These inhibitors are more prone to binding the "enzyme-substrate" complex compared to the enzyme, and they can cause configurational changes of the reverse transcriptase through interaction, attenuating the affinity of the active site to the substrate. Impressively, the non-nucleoside reverse transcriptase inhibitors will not directly damage the function of the substrate-binding domain, so they are less cytotoxic, and moreover, they can still inhibit the activity of viral reverse transcriptase even at an extremely low concentration (*Chem. Soc. Rev.*, 2012, 41, 4657-4670).

TAR and RRE are two important functional regions on HIV RNA, which play a crucial role in the reverse transcription of viral RNA (*Mol. Cell Biol.*, 1988, 8, 2555-2561). Recently, a class of aminothiazole compounds has been reported to show good TAR RNA selectivity (*Chem. Eur. J.*, 2014, 20, 2071-2079; *Chem. Commun.*, 2010, 46, 6162-6164). Specifically, these compounds can selectively bind to the U-A base pair of TAR RNA without being affected by DNA and tRNA, inhibiting the growth of HIV-1 strains. In addition, these compounds have no obvious effect on the growth of normal cells. However, such compounds do not exhibit sufficient binding ability to the TAR RNA. Therefore, there is an urgent need to develop a TAR RNA binding agent with high selectivity and high binding strength to improve the inhibition against HIV reverse transcriptase.

SUMMARY

An object of this disclosure is to provide a metalloporphyrin compound of formula (I), or an optical isomer, a pharmaceutically-acceptable salt or a solvate thereof, and a preparation and application thereof, where the metalloporphyrin compound is capable of specifically identifying the HIV RNA and effectively inhibiting the HIV reverse transcriptase.

Metalloporphyrin is found to be able to effectively select RNA as a target and effectively inhibit the activity of reverse transcriptase. As disclosed herein, a thiazole compound is creatively introduced to further optimize the molecular structure of metalloporphyrin, and the resultant metalloporphyrin compound carrying an aminothiazole functional group has good water solubility and spectral properties and high specificity to recognize HIV RNA, so that it can selectively bind to the TAR region of the HIV RNA and significantly inhibit the activity of HIV reverse transcriptase. In summary, the metalloporphyrin compound can be used not only as a specific HIV RNA binding reagent, but also as a specific inhibitor of HIV reverse transcriptase, and thus it is considered as a potential highly active and specific drug for the treatment of AIDS.

The technical solutions of this disclosure are described as follows.

In a first aspect, this disclosure provides a compound of formula (I), or an optical isomer, a pharmaceutically-acceptable salt or a solvate thereof, wherein $R_1$ is selected from the group consisting of H, OH, t-Bu, F, Cl, Br, OMe, $NMe_2$, $NO_2$ and $CH_3$; and $R_2$ is selected from the group consisting of H, t-Bu, OH, OMe, $NMe_2$, $NO_2$, F, Cl, Br and $CH_3$.

In some embodiments, $R_1$ is H, and $R_2$ is H.

In some embodiments, $R_1$ is OH, and $R_2$ is t-Bu.

In a second aspect, this disclosure provides a method for preparing the compound of formula (I), comprising:

(1) reacting a compound of formula (II) with methyl p-formylbenzoate and pyrrole under heating to produce a compound of formula (III);

(2) hydrolyzing the compound of formula (III) under an alkaline condition; adjusting the hydrolyzed product to an acidic pH to produce a compound of formula (IV);

(3) condensating the compound of formula (IV) with an aminothiazole compound under the action of 1-hydroxy-7-azobenzotriazole, 1-ethyl-carbodiimide hydrochloride and 4-dimethylaminopyridine to obtain a compound of formula (V); and (4) reacting the compound of formula (V) with zinc ion to obtain the compound of formula (I);

as shown in the following scheme:

-continued

Formula III

Formula IV

-continued

Formula V

Formula I wherein when $R_1$ is H, $R_2$ is H; and when $R_1$ is OH, $R_2$ is t-Bu.

In some embodiments, the aminothiazole compound is N-(4-(3-aminophenyl)thiazol-2-yl)acetamide.

In some embodiments, in step (1), a molar ratio of the compound of formula (II) to methyl p-formylbenzoate to pyrrole is (1-4):(0.5-1.5):(2-6), preferably 3:1:4; and/or in step (3), a molar ratio of the compound of formula (IV) to the aminothiazole compound to 1-hydroxy-7-azobenzotriazole to 1-ethyl-carbodiimide hydrochloride to 4-dimethylaminopyridine is (0.5-2):(0.5-1.5):(0.5-2):(0.5-2):(0.2-0.8), preferably 1:1.2:1:1:0.5; and/or in step (4), a molar ratio of zinc ion to the compound of formula (V) is larger than 1:1, preferably 2:1.

In some embodiments, the step (1) comprises:

dissolving the compound of formula (II) and methyl p-formylbenzoate with a first solvent; and heating the reaction mixture to 120-150° C. followed by addition of pyrrole for reaction.

In an embodiment, the first solvent is selected from the group consisting of propionic acid, butyric acid, isopropylic acid and a combination thereof, preferably propionic acid.

In an embodiment, the reaction mixture is heated to 135-145° C., preferably 140° C.

In some embodiments, the step (2) comprises:

dissolving the compound of formula (III) with a second solvent; adding a base solution to hydrolyze the compound of formula (III); adjusting the hydrolyzed product to an acidic pH to form a precipitate; and filtering the reaction mixture to collect the precipitate to obtain the compound of formula (IV).

In an embodiment, the second solvent is selected from the group consisting of tetrahydrofuran, methanol, ethanol, isopropanol, acetone, dimethyl sulfoxide, dimethyl formamide, dioxane, ethylene glycol, glycerin and a combination thereof, preferably tetrahydrofuran.

In an embodiment, the base solution is selected from the group consisting of NaOH, KOH, sodium ethoxide and potassium tert-butoxide with a concentration larger than 1 mol/L.

In an embodiment, in step (2), the reaction mixture is adjusted to pH 2-4, preferably 3.

In some embodiments, the reaction mixture is adjusted with a pharmaceutically-acceptable inorganic acid, organic acid or alkali.

In some embodiments, the inorganic acid is selected from the group consisting of hydrochloric acid, sulfuric acid, phosphoric acid and a combination thereof.

In some embodiments, the organic acid is selected from the group consisting of formic acid, acetic acid, lactic acid, aspartic acid, citric acid and a combination thereof.

In some embodiments, the step (1) further comprises:

purifying the compound of formula (III).

In some embodiments, the purification of the compound of formula (III) is carried out using an existing technique such as column chromatography.

In a third aspect, this disclosure further provides a use of the compound of formula (I), or an optical isomer, a pharmaceutically-acceptable salt or a solvate thereof in the preparation of a reagent for selectively identifying HIV TAR RNA.

In a fourth aspect, this disclosure further provides a use of the compound of formula (I), or an optical isomer, a pharmaceutically-acceptable salt or a solvate thereof in the preparation of an HIV reverse transcriptase inhibitor.

In a fifth aspect, this disclosure further provides a pharmaceutical composition, comprising;

the compound of formula (I), or an optical isomer, a pharmaceutically-acceptable salt or a solvate thereof, and one or more pharmaceutically-acceptable carriers.

The "pharmaceutically-acceptable carrier" refers to a diluent, adjuvant, excipient or vehicle administered with the therapeutic agent, which is suitable for contact with human and/or animal tissues within the a reasonable medical range without excessive toxicity, irritation, allergic reactions, or other problems or complications under a reasonable benefit-risk ratio.

Compared to the prior art, this disclosure has the following beneficial effects.

The metalloporphyrin compound provided herein has a stable structure and good spectral properties, and can selectively bind to HIV RNA and effectively inhibit the activity of HIV reverse transcriptase. The preparation of the metalloporphyrin compound has scientific process and simple operation.

This disclosure creatively introduces the thiazole compound to the molecular structure of metalloporphyrin to obtain a novel metalloporphyrin compound, which has the following advantages: (1) good water solubility and stability; (2) excellent spectral properties (generating spectral response to RNA); (3) desirable selectivity to HIV RNA; and (4) enhanced ability to inhibit the HIV reverse transcriptase compared to aminothiazole compounds.

DETAILED DESCRIPTION OF EMBODIMENTS

This disclosure will be further described below with reference to the accompanying drawings and embodiments. The embodiments are merely illustrative of the disclosure, and are not intended to limit the disclosure. Unless otherwise specified, the experiments in the embodiments are performed using conventional reagents, methods and equipment in the art to which this application pertains, and the reagents and materials used herein are all commercially available.

Example 1 Preparation of Metalloporphyrin Compound ZnTPPtz1

1. Preparation of Carboxy Porphyrin Compound TPPCOOH1

1.49 mg (9 mmol) of methyl 4-formyl benzoate and 2.76 mL (27 mmol) of benzaldehyde were dissolved in 120 mL of propionic acid in a 250 mL double-necked round-bottom flask. The reaction mixture was heated to 140° C., added with 2.5 mL of redistilled pyrrole (36 mmol) and refluxed for 2 h. After cooled to room temperature, the reaction mixture was added with 20 mL of ethanol and cooled in a refrigerator overnight, and a purple solid was generated. The reaction mixture was filtered under vacuum, and the purple solid was collected, dried and purified by column chromatography using a mixed solvent of dichloromethane and petroleum ether in a volume ratio of 2:1 to obtain 1.26 g of methyl tetraphenylporphyrincarboxylate. The product was dissolved in 80 mL of tetrahydrofuran, to which 160 mL of 1 mol/L potassium hydroxide solution was added. Then the reaction mixture was refluxed at 66° C. for 72 h. After the reaction was confirmed by TLC to be completed, the reaction mixture was adjusted to pH 3 with HCl and a purple solid was formed. The purple solid was collected by suction filtration, washed several times with 100 mL of water and dried in a vacuum oven overnight to obtain 0.92 g of TPPCOOH1 as shown in the following formula:

TPPCOOH1: R1 = H, R2 = H

2. Preparation of Metalloporphyrin Compound ZnTPPtz1

100 mg (0.15 mmol) of TPPCOOH1, 41.9 mg (0.18 mmol) of aminothiazole compound N-(4-(3-aminophenyl)thiazol-2-yl)acetamide, 20.5 mg (0.15 mmol) of HOAt and 16.8 mg (0.075 mmol) of DMAP were dissolved in 5 mL of DMF in a 25 mL single-necked round-bottom flask, to which 5 mL of DMF was dropwise added. The reaction mixture was reacted overnight at room temperature, concentrated to 5 mL under vacuum, and added with 25 mL of water, and a purple precipitate was formed. After suction filtration, the purple precipitate was collected, washed with 100 mL of water several times and dried in a vacuum oven overnight to obtain 98 mg of porphyrin TPPtz1 as shown in the following formula.

$^1$H-NMR (300 MHz, CDCl$_3$), δ (ppm): δ 12.42 (s, 1H), 10.77 (s, 1H), 8.85 (d, J=9.8 Hz, 9H), 8.68 (s, 1H), 8.44 (q, J=8.1 Hz, 5H), 8.24 (dd, J=6.7, 2.9 Hz, 7H), 7.92-7.75 (m, 11H), 7.73 (d, J=7.7 Hz, 1H), 7.62 (s, 2H), 7.54 (d, J=8.0 Hz, 2H), 2.24 (s, 3H), 2.81 (s, 2H).

TPPtz1: R1 = H, R2 = H 87.5 mg (0.1 mmol) of the porphyrin TPPtz1 was dissolved in 10 mL of a mixture of dichloromethane and ethanol in a volume ratio of 3:2, to which 36.6 mg (0.2 mmol) of anhydrous zinc acetate was added. The reaction mixture was reacted at room temperature for 12 h, and then evaporated under vacuum to obtain a crude product. The crude product was dissolved in 5 mL of DMSO, to which 25 mL of water was added, and a purple precipitate was formed. After suction filtration, the purple precipitate was collected, washed with 100 mL of water several times and then dried in a vacuum oven overnight to obtain 86 mg of the desired metalloporphyrin compound ZnTPPtz1.

$^1$H-NMR (300 MHz, CDCl$_3$), δ (ppm): δ 12.42 (s, 1H), 10.77 (s, 1H), 8.85 (d, J=9.8 Hz, 9H), 8.68 (s, 1H), 8.44 (q, J=8.1 Hz, 5H), 8.24 (dd, J=6.7, 2.9 Hz, 7H), 7.92-7.75 (m, 11H), 7.73 (d, J=7.7 Hz, 1H), 7.62 (s, 2H), 7.54 (d, J=8.0 Hz, 2H), 2.24 (s, 3H).

boxylate. The product was dissolved in 50 mL of tetrahydrofuran, added with 100 mL of 1 mol/L potassium hydroxide solution and refluxed at 66° C. for 72 h. After the reaction was confirmed by TLC to be completed, the reaction mixture was adjusted to pH 3 with HCl, and a purple solid was formed. After suction filtration, the purple solid was collected, washed with 100 mL of water several times and dried in a vacuum oven overnight to obtain 1.04 g of TPPCOOH2.

$^1$H-NMR (300 MHz, CDCl$_3$), δ (ppm): δ 8.94 (d, J=4.9 Hz, 6H), 8.79 (d, J=4.8 Hz, 2H), 8.48 (d, J=8.2 Hz, 2H), 8.36 (d, J=8.2 Hz, 2H), 8.04 (s, 6H), 5.55 (s, 3H), 1.62 (s, 54H), 2.71 (s, 2H).

ZnTPPtz1: R1 = H, R2 = H

Example 2 Preparation of Metalloporphyrin Compound ZnTPPtz2

1. Preparation of Carboxy Porphyrin Compound TPPCOOH2

3.5 mg (15 mmol) of 3,5-di-tert-butyl-4-hydroxybenzaldehyde and 0.83 g (5 mmol) of methyl 4-formyl benzoate were dissolved in 120 mL of propionic acid in a 250 mL double-necked round-bottom flask. The reaction mixture was heated to 140° C., added with 1.4 mL (20 mmol) of redistilled pyrrole and refluxed for 2 h. After cooled to room temperature, the reaction mixture was added with 20 mL of ethanol and cooled in a refrigerator overnight, and a purple solid was generated. After suction filtration, the purple solid was collected, dried and purified by column chromatography using a mixed solvent of dichloromethane and petroleum ether in a volume ratio of 2:1 to obtain 1.1 g of methyl tert-butyl hydroxyl-substituted tetraphenylporphyrin car- TPPCOOH2: R1 = OH, R2 = t-Bu 4. Preparation of Metalloporphyrin Compound ZnTPPtz2

156 mg (0.15 mmol) of TPPCOOH2, 41.9 mg (0.18 mmol) of aminothiazole compound N-(4-(3-aminophenyl)thiazol-2-yl)acetamide, 20.5 mg (0.15 mmol) of HOAt and 16.8 mg (0.075 mmol) of DMAP were dissolved in 5 mL of DMF in a 25 mL single-necked round-bottom flask, to which 5 mL of DMF was dropwise added. The reaction mixture was reacted overnight at room temperature, concentrated to 5 mL under vacuum and added with 25 mL of water, and a purple precipitate was formed. After suction filtration, the precipitate was washed with 100 mL of water several times and dried in a vacuum oven overnight to obtain 149 mg of porphyrin TPPtz2 as shown in the following formula.

$^1$H-NMR (300 MHz, CDCl$_3$), δ (ppm): δ 9.90 (s, 1H), 8.94 (d, J=1.9 Hz, 6H), 8.78 (d, J=4.8 Hz, 2H), 8.49-8.16 (m, 5H), 8.03 (s, 6H), 7.75 (d, J=8.1 Hz, 1H), 7.66 (d, J=7.8 Hz, 1H), 7.49 (t, J=7.9 Hz, 1H), 5.54 (s, 3H), 2.23 (s, 3H), 1.62 (d, J=1.5 Hz, 55H), −2.68 (s, 2H).

TPPtz3: R1 = OH, R2 = t-Bu 104 mg (0.1 mmol) of the porphyrin TPPtz2 was dissolved in 10 mL of a mixture of dichloromethane and ethanol in a volume ratio of 3:2, to which 36.6 mg (0.2 mmol) of anhydrous zinc acetate was added. The reaction mixture was reacted at room temperature for 12 h and subjected to rotary evaporation under vacuum to remove the solvent to obtain a crude product. The crude product was dissolved in 5 mL of DMSO, to which 25 mL of water was added, and a purple precipitate was formed. After suction filtration, the precipitate was collected, washed with 100 mL of water several times and dried in a vacuum oven overnight to obtain 102 mg of the metalloporphyrin compound ZnTPPtz2.

$^1$H-NMR (300 MHz, DMSO-d6), δ (ppm): δ 12.36 (s, 1H), 10.71 (s, 1H), 8.89 (d, J=4.0 Hz, 6H), 8.80 (d, J=4.7 Hz, 2H), 8.65 (t, J=1.8 Hz, 1H), 8.40 (q, J=8.0 Hz, 4H), 7.95 (d, J=4.3 Hz, 6H), 7.80 (d, J=8.5 Hz, 1H), 7.69 (d, J=7.5 Hz, 1H), 7.59 (s, 1H), 7.50 (d, J=7.9 Hz, 1H), 7.39 (d, J=2.2 Hz, 3H), 2.21 (s, 3H), 1.60 (s, 55H).

ZnTPPtz2: R1 = OH, R2 = t-Bu

Example 3 Investigation of Binding Ability of Metalloporphyrin Compound to HIV TAR RNA The binding ability of the metalloporphyrin compounds prepared herein to HIV TAR RNA was tested by electrophoresis.

Figure 1:
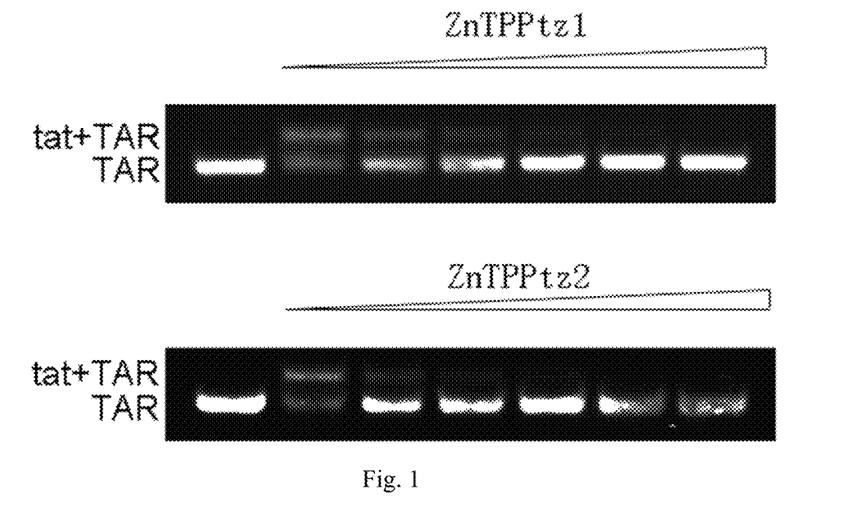
FIG. 1 is a gel electrophoretogram schematically depicting the binding of trans-activator (tat) to TAR RNA under different concentrations of a metalloporphyrin compound according to an embodiment of this disclosure.

The HIV TAR RNA (Shanghai Sangon Biotech Co., Ltd.) and the TAR binding protein tat (Chinapeptides Biotechnology Co., Ltd., Shanghai) were separately dissolved with 50 mM Tris buffer (pH 7.3) to prepare a 0.1 mM solution. Several wells of a microplate were selected as test wells, which were individually added with 4 μL of the TAR RNA solution and 4 μL of the tat solution, and the microplate was incubated at 37° C. for 1 h. After that, each test well was added with 12 μL of water or different concentrations of the metalloporphyrin compound such that the reaction mixture had a total volume of 20 μL. The microplate was incubated at 37° C. for 1 h, and then 8 μL of the reaction mixture was taken, mixed with 2 μL of bromophenol blue loading buffer and analyzed by polyacrylamide gel electrophoresis. Then the gel was stained with 4S Gel Red and imaged on FluorChemFC3. As shown in FIG. 1, the concentration of the metalloporphyrin compound was 0, 5, 10, 20, 40 and 80 μM in sequence from left to right, and as the concentration of the metalloporphyrin compound increased, fewer and fewer tat proteins were bound to the TAR RNA, and eventually there was no TAR RNA bound with the tat protein. The experimental results indicated that the metalloporphyrin compound competed with the tat for binding to the same site. By contrast, the compound ZnTPPtz2 had a significantly stronger ability to bind the TAR RNA than ZnTPPtz1, which indicated that the tertiary butyl with relatively large steric hindrance can provide a more specific space for the interaction between the TAR RNA and Zn ions, allowing for enhanced binding ability to the TAR RNA.

Figure 2:
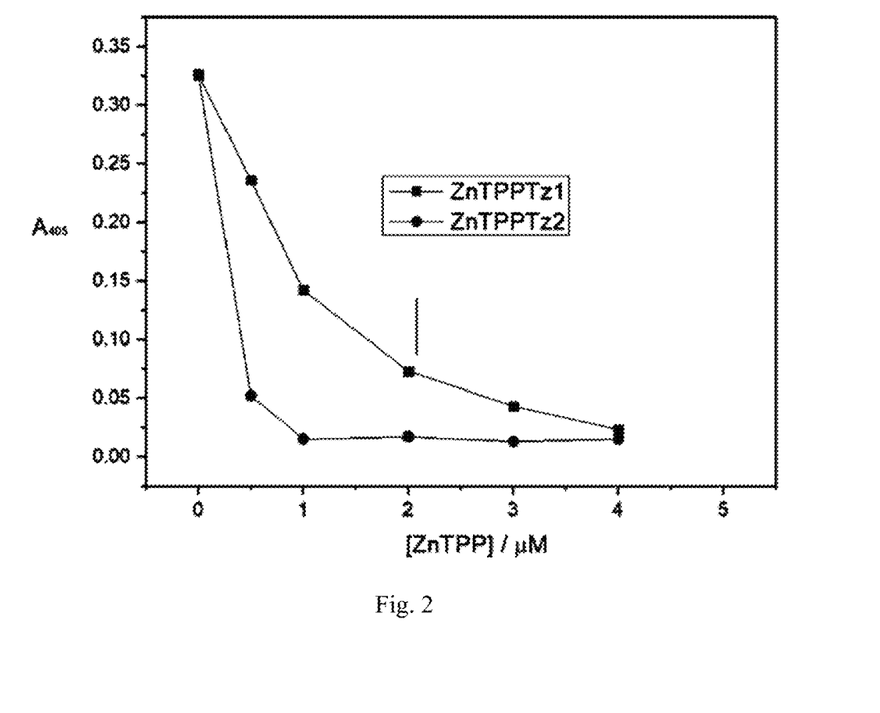
FIG. 2 shows inhibitory effect of the metalloporphyrin compound on HIV reverse transcriptase (tested by ELISA).
Figure 3A:
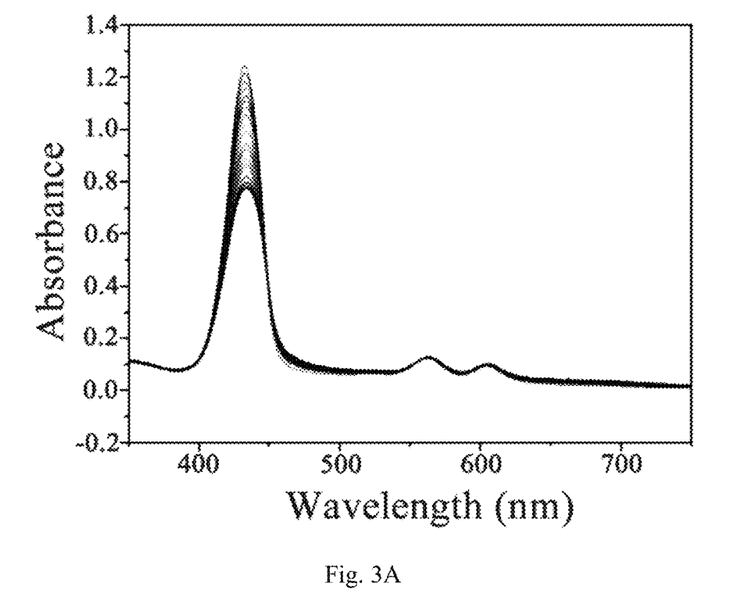
FIGS. 3A-3D are ultraviolet-visible spectrums respectively showing interactions of the metalloporphyrin compound ZnTPPtz1 with DNA (3A), total RNA (3B), tRNA (3C) and poly(A)RNA (3D).
Figure 3B:
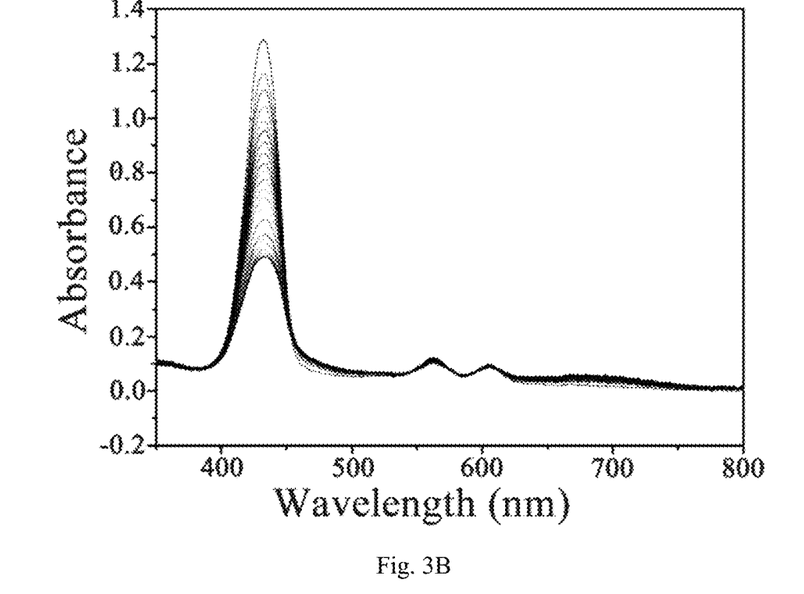
Figure 3C:
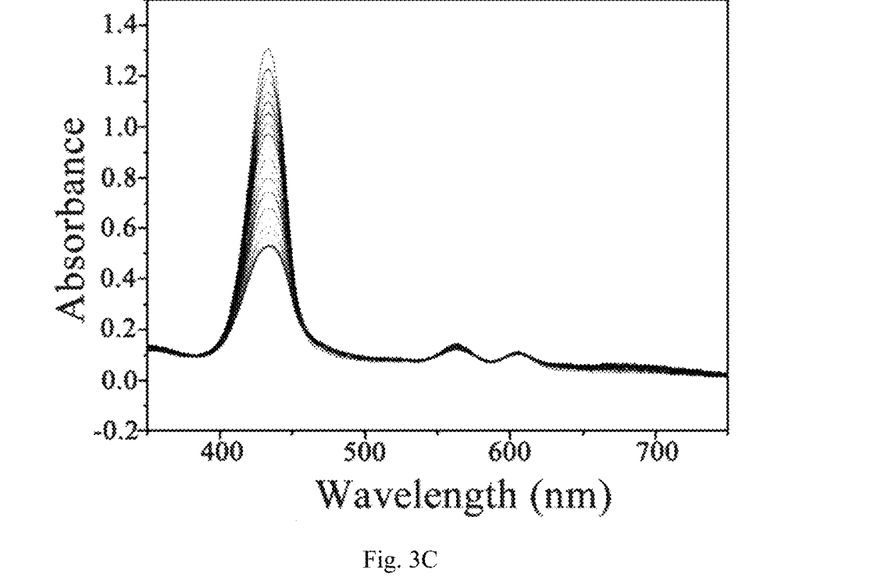
Figure 3D:
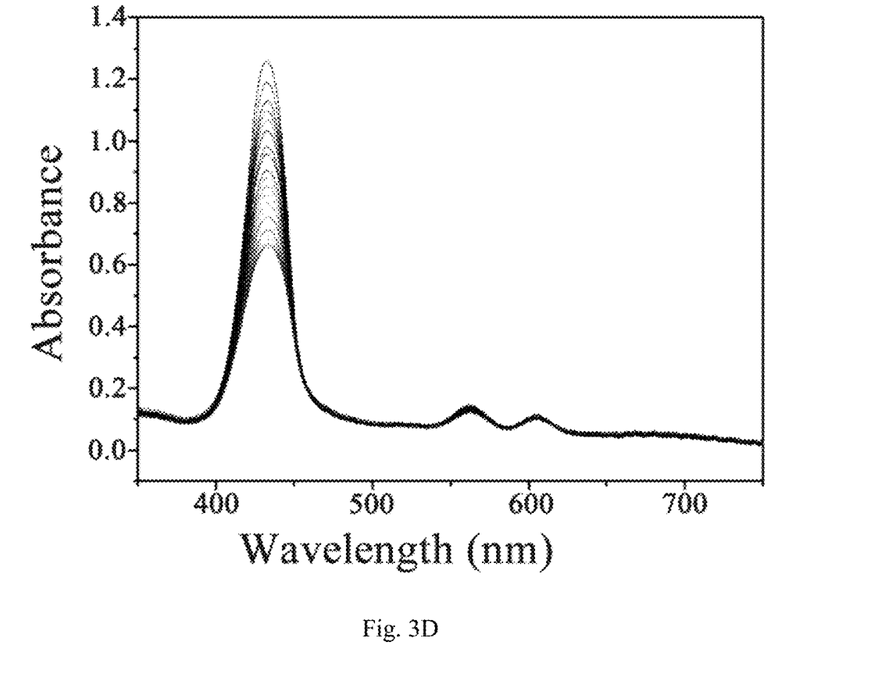
Figure 4A:
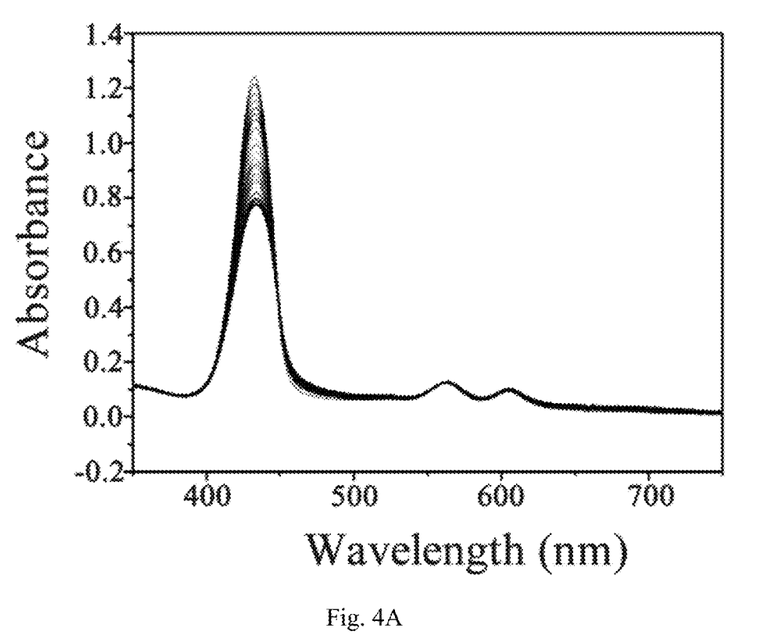
FIGS. 4A-4D are ultraviolet-visible spectrums respectively showing interactions of the metalloporphyrin compound ZnTPPtz2 with DNA (3A), total RNA (3B), tRNA (3C) and poly(A)RNA (3D).
Figure 4B:
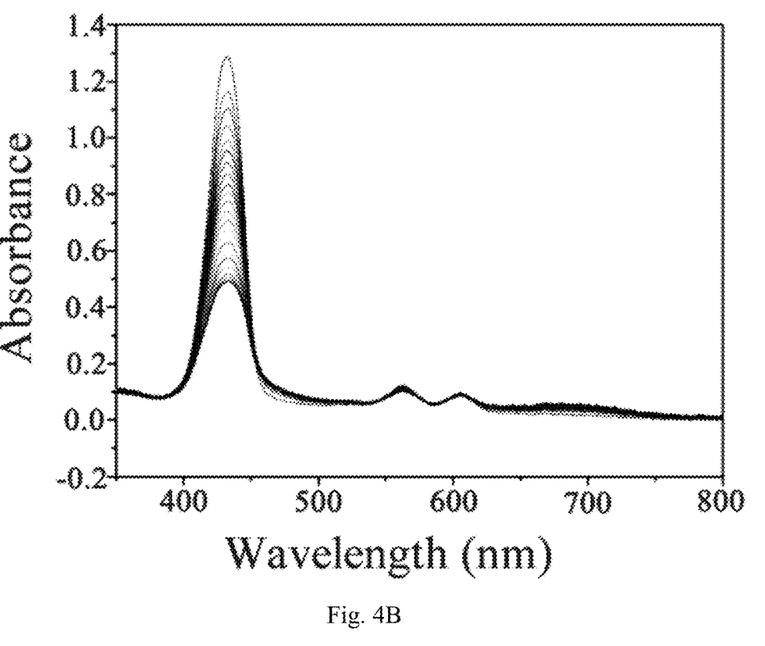
Figure 4C:
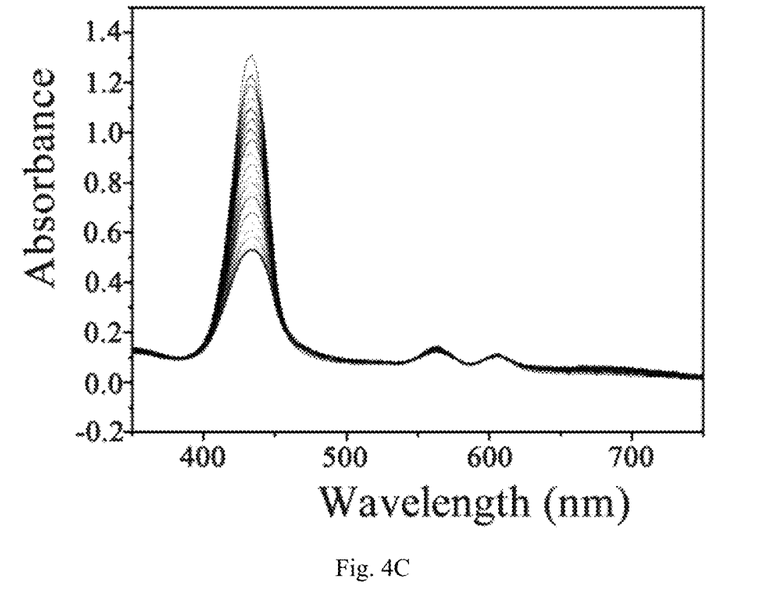
Figure 4D:
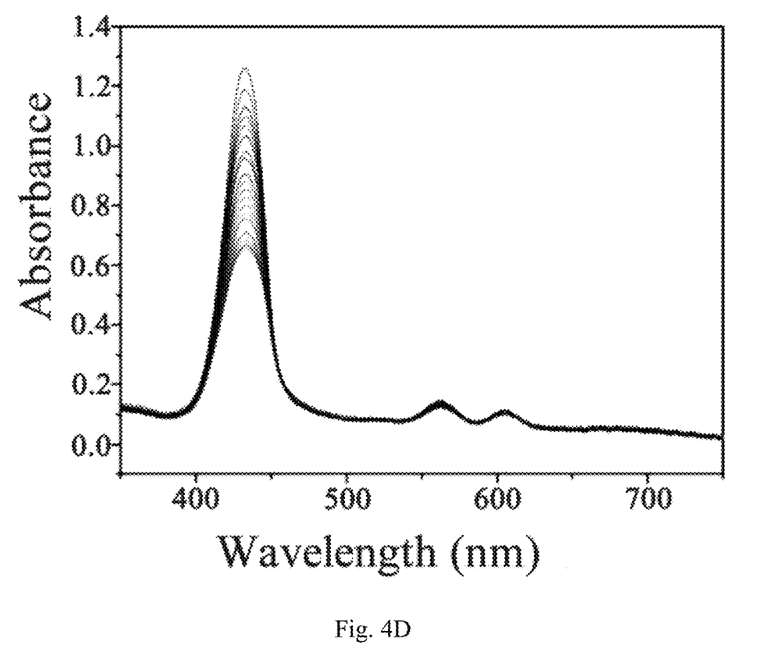

Example 4 Investigation on Inhibitory Effect of Metalloporphyrin Compounds on HIV Reverse Transcriptase The inhibitory activity of the metalloporphyrin compound against the recombinant HIV-1 reverse transcriptase was tested by enzyme-linked immunosorbent assay (ELISA) using the Roche kit (Reverse Transcriptase Assay, colorimetric) based on an. 5 ng of recombinant HIV-1 reverse transcriptase was added into a well of a microplate and diluted with 20 μL of a lysis buffer. Another well was added with the lysis buffer free of the recombinant HIV-1 reverse transcriptase and used as negative control. 20 μL of the metalloporphyrin compound diluted in lysis buffer and 20 μL of a reaction mixture (46 mM of Tris, 266 mM of potassium chloride, 27.5 mM of magnesium chloride, 9.2 mM of dithiothreitol, 10 μM of dUTP/dTTP, 0.75 $A_{260}$/mL template poly(A)/primer$(dT)_{15}$) were added to each well and the microplate was incubated at 37° C. for 1 h. Each of the above reaction systems (60 μL) was transferred to an ELISA strip and covered with a cover foil, and incubated at 37° C. for 1 h. The liquid in each well was removed thoroughly, and then each well was washed five times with 250 μL of a washing buffer each for 30 s, and then the washing buffer was carefully removed. Subsequently, each well was added with 200 μL of an anti-DIG-POD working solution (200 mU/mL), covered with a cover foil and incubated at 37° C. for 1 h. The liquid was poured out thoroughly, and each well was washed five times with 250 μL of the washing buffer each for 30 s. After the washing buffer was carefully removed, each well was added with 200 μL of ABTS (2, 2'-azino-bis(3-ethylbenzothiazoline-6-sulfonic acid) diammonium salt) substrate solution, incubated at 25° C. and subjected to photometric detection until obvious color change (green) was observed (10-30 min), where the photometric detection was performed at 405 nm (reference wavelength: about 490 nm) using an ELISA reader. The results were shown in FIG. 2, and through the single exponential fitting, IC50 of metalloporphyrin compounds ZnTPPtz1 and ZnTPPtz1 against the HIV reverse transcriptase activity was 1.25 and 0.23 μM, respectively, which were significantly lower than that of the existing aminothiazole compounds unbound to the metalloporphyrin compound. Therefore, the metalloporphyrin compound prepared herein had high HIV reverse transcriptase inhibitory activity, which was considered as a potential drug for the treatment of reverse transcriptase-related diseases such as AIDS.

Example 5 Investigation on Interaction Between Metalloporphyrin Compound and Nucleic Acids

20 mg of calf thymus DNA, total RNA, yeast tRNA, and poly(A) RNA were respectively dissolved in 4 mL of Tris-NaCl buffer (5 mM Tris, 50 mM NaCl, pH 7.0) and ultrasonicated for 15 min. Each solution was filtered to obtain a filtrate, which was diluted as needed to measure the absorbance at 260 nm and 280 nm, where a value of $A_{260}/A_{280}$ within the range of 1.8-1.9 indicated that there was basically no protein and RNA. The absorbance ($A_{260}$) of the calf thymus DNA was measured at 260 nm using an ultraviolet-visible spectrophotometer, and the molar extinction coefficient value 6600 $M^{-1}$ $cm^{-1}$. In this case, the concentration of calf thymus DNA was calculated according to $[DNA]=K \cdot A_{260}/6600$, where K is the dilution factor, M. The concentration was finally converted to the concentration of CT-DNA stock solution. The concentrations of poly(A) RNA, total RNA, and yeast tRNA were determined according to the above method, where the molar extinction coefficient values were 10100 $M^{-1}$ $cm^{-1}$, 8000 $M^{-1}$ $cm^{-1}$, and 7700 $M^{-1}$ $cm^{-1}$, respectively. The metalloporphyrin compounds ZnTPPtz1 and ZnTPPtz2 were also prepared into a 10 μM solution using Tris-NaCl buffer, respectively, which was added with a certain volume of the DNA or RNA solution by a micropipettor to increase the concentration ratio of nucleic acid to metalloporphyrin compound in a certain proportion until the peak value did not change after the dilution effect was deducted. After mixed uniformly for 3 min each time, the reaction mixture was measured throughout the range of 200-800 nm to record the changes of the ultraviolet spectrum of the metalloporphyrin compound. The ultraviolet spectrums depicting interactions between the metalloporphyrin compound ZnTPPtz1 and the four nucleic acids were shown in FIGS. 3A-3D, and the ultraviolet spectrums depicting interactions between the metalloporphyrin compound ZnTPPtz2 and the four nucleic acids were shown in FIGS. 4A-4D. It can be concluded from these figures that the hypochromic effect of the metalloporphyrin compound ZnTPPtz2 was stronger than that of ZnTPPtz1, especially with respect to the three RNA samples, which indicated that ZnTPPtz2 can more effectively bind to RNA.

The metalloporphyrin compound provided herein was capable of specifically binding to RNA and recognizing the binding site of tat protein on the HIV TAR RNA to effectively inhibit the activity of HIV reverse transcriptase. Therefore, the metalloporphyrin compound provided herein was promising for the treatment of reverse transcriptase-related diseases such as AIDS.

The above are only the preferred embodiments of this disclosure, and are not intended to limit the scope of this disclosure. Any changes, modifications and improvements made by those skilled in the art without departing from the spirit of this disclosure shall fall within the scope of this disclosure.

What is claimed is:

1. A compound of formula (I), or a pharmaceutically-acceptable salt thereof wherein the compound of formula (I) have (a) H for $R_1$ and $R_2$ or (b) OH for $R_1$ and t-Bu for $R_2$.

2. A method for preparing the compound of formula (I), comprising:

(1) reacting a compound of formula (II) with methyl p-formylbenzoate and pyrrole under heating to produce a compound of formula (III);

(2) hydrolyzing the compound of formula (III) under an alkaline condition; adjusting the hydrolyzed product to an acidic pH to produce a compound of formula (IV);

(3) condensating the compound of formula (IV) with an aminothiazole compound under the action of 1-hydroxy-7-azobenzotriazole, 1-ethyl-carbodiimide hydrochloride and 4-dimethylaminopyridine to obtain a compound of formula (V); and

(4) reacting the compound of formula (V) with zinc ion to obtain the compound of formula (I);

as shown in the following scheme:

Formula V

Formula I wherein the compound of formula (I) have
(a) H for R₁ and R₂
or
(b) OH for R₁ and t-Bu for R₂.

3. The method of claim 2, wherein in step (1), a molar ratio of the compound of formula (II) to methyl p-formylbenzoate to pyrrole is (1-4):(0.5-1.5):(2-6).

4. The method of claim 3, wherein in step (1), a molar ratio of the compound of formula (II) to methyl p-formylbenzoate to pyrrole is 3:1:4.

5. The method of claim 2, wherein the step (1) comprises:
dissolving the compound of formula (II) and methyl p-formylbenzoate with a first solvent; and heating the reaction mixture to 120-150° C. followed by addition of pyrrole for reaction; and the step (2) comprises:
dissolving the compound of formula (III) with a second solvent; adding a base solution to hydrolyze the compound of formula (III); adjusting the hydrolyzed product to an acidic pH to form a precipitate; and filtering the reaction mixture to collect the precipitate to obtain the compound of formula (IV).

6. The method of claim 5, wherein the first solvent is selected from the group consisting of propionic acid, butyric acid, isopropylic acid and a combination thereof.

7. The method of claim 6, wherein the first solvent is propionic acid.

8. The method of claim 5, wherein the reaction mixture is heated to 135-145° C.

9. The method of claim 8, wherein the reaction mixture is heated to 140° C.

10. The method of claim 5, wherein the second solvent is selected from the group consisting of tetrahydrofuran, methanol, ethanol, isopropanol, acetone, dimethyl sulfoxide, dimethyl formamide, dioxane, ethylene glycol, glycerin and a combination thereof.

11. The method of claim 10, wherein the second solvent is tetrahydrofuran.

12. The method of claim 5, wherein the base solution is selected from the group consisting of NaOH and KOH with a concentration larger than 1 mol/L.

13. The method of claim 5, wherein the reaction mixture is adjusted to pH 2-4.

14. The method of claim 13, wherein the reaction mixture is adjusted to pH 3.

15. A method of inhibiting human immunodeficiency virus (HIV) reverse transcriptase, comprising: contacting a human or animal tissue with the compound of claim 1.

16. A pharmaceutical composition, comprising:
the compound of claim 1, or a pharmaceutically-acceptable salt thereof; and
one or more pharmaceutically-acceptable carriers.

17. The method of claim 2, wherein in step (3), a molar ratio of the compound of formula (IV) to the aminothiazole compound to 1-hydroxy-7-azobenzotriazole to 1-ethyl-carbodiimide hydrochloride to 4-dimethylaminopyridine is (0.5-2):(0.5-1.5):(0.5-2):(0.5-2):(0.2-0.8).

18. The method of claim 17, wherein in step (3), a molar ratio of the compound of formula (IV) to the aminothiazole compound to 1-hydroxy-7-azobenzotriazole to 1-ethyl-carbodiimide hydrochloride to 4-dimethylaminopyridine is 1:1.2:1:1:0.5.

19. The method of claim 2, wherein in step (4), a molar ratio of zinc ion to the compound of formula (V) is larger than 1:1.

20. The method of claim 19, wherein in step (4), a molar ratio of zinc ion to the compound of formula (V) is 2:1.

* * * * *